(12) United States Patent
Dietschi et al.

(10) Patent No.: US 7,571,621 B2
(45) Date of Patent: Aug. 11, 2009

(54) FLUID COOLING SYSTEM, COOLED FLUID DISPENSER COMPRISING THE LATER, AND METHODS FOR STERILIZATION THEREOF

(75) Inventors: Eric Dietschi, Chardonne (CH); Eric Fournier, Broutvernet (FR); Alexandre Pereira, Cebazat (FR)

(73) Assignee: Dieau S.A., Cebazat (FR)

( * ) Notice: Subject to any disclaimer, the term of this patent is extended or adjusted under 35 U.S.C. 154(b) by 101 days.

(21) Appl. No.: 10/539,911

(22) PCT Filed: Dec. 17, 2003

(86) PCT No.: PCT/IB03/06059

§ 371 (c)(1),
(2), (4) Date: Jun. 16, 2005

(87) PCT Pub. No.: WO2004/055458

PCT Pub. Date: Jul. 1, 2004

(65) Prior Publication Data

US 2006/0123830 A1 Jun. 15, 2006

(30) Foreign Application Priority Data

Dec. 18, 2002 (EP) .................................. 02293148

(51) Int. Cl.
*F25D 17/02* (2006.01)

(52) U.S. Cl. ................. 62/434; 165/141; 62/59

(58) Field of Classification Search ............... 62/59, 62/434–435; 165/140–141
See application file for complete search history.

(56) References Cited

U.S. PATENT DOCUMENTS

| 4,916,910 A * | 4/1990 | Schroeder ................. 62/59 |
| 5,140,824 A * | 8/1992 | Hunt ....................... 62/59 |
| 6,095,240 A * | 8/2000 | Hassanein et al. ......... 165/141 |
| 6,216,469 B1 * | 4/2001 | Miller ..................... 62/59 |
| 6,497,183 B2 * | 12/2002 | Demarquilly et al. ... 105/392.5 |
| 6,581,405 B2 * | 6/2003 | Kim et al. ................ 62/476 |

FOREIGN PATENT DOCUMENTS

| RU | 1377244 | 2/1988 |
| RU | 1530161 | 12/1989 |

* cited by examiner

*Primary Examiner*—William E Tapolcai
(74) *Attorney, Agent, or Firm*—Hoffman & Baron, LLP; Irving N. Feit

(57) ABSTRACT

The present invention relates to a fluid cooling system (1), for use in dispensing or distributing a chilled or cooled fluid, comprising a primary heat exchanger system (2), a secondary heat exchanger system (3), a first conduit (9) through which fluid to be cooled or chilled is circulated, and a heat transfer agent (8) for transferring cooling energy to the fluid to be chilled circulating in the first conduit (9), wherein the primary and secondary heat exchanger systems (2, 3) are arranged at least partially one inside of another The invention also relates to cooled fluid dispensers incorporating the fluid cooling system and a methods for sterilization thereof.

54 Claims, 4 Drawing Sheets

FLUID COOLING SYSTEM, COOLED FLUID DISPENSER COMPRISING THE LATER, AND METHODS FOR STERILIZATION THEREOF

FIELD OF THE INVENTION

The present invention relates to fluid cooling systems and cooled fluid dispensers. In particular, the present invention will be described and explained in relation to cooled beverage dispensers, such as water dispensers, commonly used for dispensing cooled or chilled drinking water or other chilled beverages.

BACKGROUND OF THE INVENTION

Fluid cooling systems adapted for use in cooled fluid dispensers are generally known from applicant's prior published applications EP 1 129 024 and U.S. Pat. No. 6,442,960. In such systems, it is usual to find a primary heat exchanger system and a secondary heat exchanger system, with a heat transfer agent being cooled in the primary exchanger system. A conduit for fluid flow is also present through which circulates a fluid to be dispensed after cooling. Such cooling is effected by bringing the conduit containing the fluid to be dispensed into direct or indirect contact with the heat transfer agent that has previously been cooled by the primary heat exchanger system.

One of the problems of the known systems is that the primary and secondary heat exchanger systems have to be quite voluminous in order to obtain the desired cooling effect of the liquid. This limits their application to chilled fluid dispensers that are in turn voluminous, and costly to run, cleanse or sterilize and maintain, and machine downtime during the cleansing or sterilization step is relatively high.

SUMMERY OF THE INVENTION

With a view to overcoming these problems, it is therefore one object of the present invention to provide a fluid cooling system, for example for use in dispensing or distributing a chilled or cooled fluid, comprising a primary heat exchanger system, a secondary heat exchanger system, a first conduit through which fluid to be cooled or chilled is circulated, and a heat transfer agent for transferring cooling energy to the fluid to be chilled circulating in the first conduit, wherein the primary and secondary heat exchanger systems are arranged at least partially one inside of another.

Another object of the invention is a cooled or chilled fluid dispenser, incorporating a fluid cooling system as described above.

Still yet another object of the present invention is a sterilization process for the fluid cooling system, and chilled fluid dispenser.

In accordance with the objects of the invention outlined above, the applicant has found a way of reducing the volume of such fluid cooling systems, while at the same maintaining the same or equivalent cooling efficiency, and increasing the ease with which the system and dispenser in which such systems are incorporated, can be maintained, viz. cleansed or sterilized. This opens up the applications of such fluid cooling and dispensing systems to other uses for which they were previously unsuitable or economically unviable, such as for dispensing cooled or chilled gaseous phase fluids, and for enabling such cooled fluids to flow through a sterilized circuit, e.g. in personal or domestic oxygen distribution appliances for respiratory assistance.

More particularly, the applicant, through the present invention have managed to reduce the volumes of heat transfer agent being circulated, and preferably also the volume of solid phase of heat transfer agent generated. This enables a reduction in the overall size of the fluid cooling system, and correspondingly any cooled or chilled fluid dispensing system into which it is incorporated. It is to be noted that the fluid cooling system of the present invention does not necessitate the presence of primary heat source in the primary heat exchanger as described in applicants prior application. Moreover, heat exchange is vastly improved with the arrangement as proposed in the present invention.

Consequently, one advantage of the present invention is that the fluid cooling system can be integrated into any chilled fluid dispenser system, such as a drinking water dispenser. Furthermore, the fluid cooling system does not need to have a drainage pump, where sterilization of the fluid cooling system or cooled fluid dispenser is not required. This is optional in the event that sterilization of the circuit including the first conduit is desired, for example, in a drinking water dispenser, or for distributing oxygen in a respiratory assistance apparatus.

In a more preferred embodiment of the invention, the primary heat exchanger system is arranged at least partially, and more preferably substantially, within the secondary heat exchanger system. By the term "partially" or "substantially within", it is meant that at least part, and preferably a major part, of the primary heat exchanger system is spatially located within the secondary heat exchanger system. This provides for a very compact fluid cooling system according to the invention and reduces the volumes of heat transfer agent that need to be circulated to obtain the desired cooling effect.

In one preferred embodiment of the present invention, the primary heat exchanger system comprises a chamber. The chamber is generally made of a plastic or metallic material, that will not deform or buckle under the operating temperatures or pressures, in particular in relation to the cold temperatures generated, and can be generally cylindrical in shape, although other shapes could be envisaged easily by the skilled person that would still be functional. The chamber is dimensioned to receive a coil, which coil serves to effect cooling thermal exchange with a heat transfer agent in the chamber of said primary heat exchanger system. It will be understood that other means of generating a cooling effect, for example, using a finger and the Pelletier effect, or equivalent means can be used, instead of the coil. Advantageously, the primary heat exchanger system also comprises a thermostat, that enables regulation of the temperature of the heat transfer agent, thereby controlling the volume of solid phase of the heat transfer agent that forms in the chamber. The terms "heat transfer agent" and "heat exchange agent" are used interchangeably in the present specification and claims and have the meaning as defined hereafter. By "heat transfer agent" or "heat exchange agent", it is meant an agent that can effectively transmit its thermal energy to the fluid to be cooled and dispensed, preferably without the necessity for an important initial energy input. Preferred heat transfer agents are ones that undergo liquid/solid phase transition. Water is the preferred heat transfer agent in this case, since the ice formed by the coil when water in the chamber comes into contact with the coil tends to only thaw again slowly, thus releasing its cooling energy over time, and only requires minimal energy input at the start. In addition, the use of water as heat transfer agent enables ice/water slurries to be circulated around the system for greater energy transfer efficiency should the need arise. Of course, other heat transfer agents that are commonly known could also be used, for example, halocarbons, such as fluorochlorocarbons, or hydrohalocarbons, solutes, solutions or dispersions that are involved in endothermic reactions by the addition or extraction of water or another solvent, gaseous heat transfer agents, such as ammonia, or any heat transfer agents in which endothermic reactions are involved and the like, that will all cause loss of heat energy from the liquid to be cooled. Other suitable heat transfer agents are monoethylene glycol, monopropylene glycol, and salt water containing anti-corrosion agents.

In the preferred embodiment, the heat transfer agent circulates within the chamber of the primary heat exchanger system and between and around the coil, which is set to withdraw heat from the heat transfer agent, and where the latter is water, cause the liquid to become partially solid and turn into ice. Such a system is typically known as an ice bank. The volume of ice is controlled by the thermostat, that is suitably positioned within the chamber, for example inside the periphery defined by the coil, or alternatively the thermostat can be placed in the chamber at another location in the chamber, depending on the degree of precision required in controlling the volume of solid phase formation of the heat transfer agent.

In the preferred embodiment of the present invention, the secondary heat exchanger system also comprises a chamber. This chamber substantially surrounds the chamber of the primary heat exchanger system, such that the latter system is substantially located within the chamber of the secondary heat exchanger system. It will be understood that the chamber of the secondary heat exchanger system is generally adapted in shape and size to receive the chamber from the primary heat exchanger system, and thus is most preferably generally cylindrical in shape, but of a greater diameter than that of the chamber of the primary heat exchanger system.

Preferably, the chamber of the primary heat exchanger system has an outlet for the heat transfer agent which communicates with the chamber of the secondary heat exchanger system. The outlet of the chamber of the primary heat exchanger system is even more preferably located in a wall of said chamber that is in contact with the chamber of the secondary heat exchanger system. Most preferably, the outlet is located in an end wall of the cylindrically shaped chamber. In this way, the heat transfer agent can circulate from the primary heat exchanger system to the secondary heat exchanger system via the outlet in the end wall of the chamber of the primary heat exchanger system.

According to a particularly preferred embodiment of the present invention, the first conduit carrying the fluid to be cooled or chilled is located within the chamber of the secondary heat exchanger system. More preferably, the first conduit carrying the fluid to be cooled is arranged as a coil within the chamber and around a peripheral wall thereof, so that in effect, it is sandwiched between the outer peripheral wall of the chamber of the primary heat exchanger, and the inner peripheral wall of the chamber of the secondary heat exchanger, there being enough space between the two chambers and the first conduit for heat transfer agent to circulate.

Preferably, the cooled heat transfer agent exiting via the outlet into the chamber of the secondary heat exchanger system flows into said chamber at one end of the chamber, over a peripheral surface of the first conduit, and out of said chamber via an outlet in a wall of said chamber at another end of the chamber of the secondary heat exchange system. The volume of heat transfer agent in the chamber of the primary heat exchanger system is such that upon phase change from liquid to solid or from gas to solid, the remaining unsolidified but cooled volume is displaced out of the chamber of the primary heat exchanger system and into the chamber of the secondary heat exchanger system. The cooled liquid or gaseous heat transfer agent that is displaced then flows over the first conduit as described, and as it comes into contact with the first conduit carrying the fluid to be cooled or chilled, warms up and is withdrawn via the outlet provided at the other end of the chamber in the secondary heat exchanger system. In this way, the fluid being carried or circulated within the first conduit is cooled or chilled.

Advantageously, and preferably, the fluid cooling system also comprises a reservoir for the heat transfer agent, located adjacent to the chamber of the secondary heat exchanger system. More preferably, the reservoir is located at a point higher than, or above, the chamber of the secondary heat exchanger system. The reservoir for the heat transfer agent can optionally be fitted with a plug comprising a membrane allowing any excess pressure created by the liquid/solid or gas/solid phase change to be vented out of the system. The reservoir can also be optionally connected to a drainage pump enabling one or more chambers to be drained of heat transfer agent for the purpose of sterilizing the first conduit. In this case, the reservoir is connected to the outlet of the chamber of the secondary heat exchanger system via the pump.

Additionally, and preferably, a second pump is provided to assist in circulating the heat transfer agent from one chamber to another, and is preferably located at or near the heat transfer agent outlet of the chamber of the secondary heat exchanger system. This pump functions while fluid is being circulated in the chambers and can be stopped, if desired, before any drainage of the fluid cooling system occurs. The first pump and second pump are preferably both connected to the outlet provided in the wall of the chamber of the secondary heat exchanger system. Thus, in this way, the reservoir is also connected to the chamber of the secondary heat exchanger system via the first pump.

In an alernatively preterred embodiment, the primary heat exchanger system is arranged at least partially, and more preferably substantially, around the secondary heat exchanger system. In this embodiment, the primary heat exchanger system comprises a second conduit that extends with and around the first conduit of the secondary heat exchanger, for at least part of the length of said first conduit. The second conduit carries the heat exchange agent originating from the primary heat exchanger. Preferably, the second conduit of the primary heat exchanger is arranged around and along the length the first conduit of the secondary heat exchanger in such a way that sufficient cooling energy is imparted by the heat exchange agent to cool the fluid circulating within conduit. Most preferably, the second conduit of the primary heat exchanger system extends coaxially along substantially the whole of the length of the first conduit of the secondary heat exchanger system. Alternatively, the second conduit of the primary heat exchanger system is coiled around the periphery of the first conduit of the secondary heat exchanger system. In yet another preferred alternative, the second conduit is arranged around the first conduit in one or more sections, such that heat transfer would occur from second conduit to first conduit at one or more non-contiguous regions or zones along the length of the first conduit, in a manner sufficient to effect desired cooling of the fluid within the first conduit. In the alternately preferred embodiment, the primary heat exchanger system comprises a separate coil and chamber for transferring cooling energy to the heat transfer agent, distant from the second conduit. In other words, the primary heat exchanger system has a distinct energy transfer unit for cooling the heat transfer agent that is located at a distance from the second conduit of the secondary heat exchanger system. In such a case, the primary heat exchanger also comprises a thermostat for regulating the temperature of the the heat transfer agent, and hence the liquid to be cooled.

As defined in the present specification and claims, the term thermostat is understood to mean electronic or electromechanical temperature sensors or detectors, or bimetallic strips for example. More preferably, the primary heat exchanger system also comprises a pump connected to the chamber of the primary heat exchanger system. The pump facilitates circulation of the heat transfer agent to the secondary heat exchanger system. The chamber of the primary heat exchanger system can be connected to the second conduit of the primary heat exchanger system via an outlet leading from said chamber to said second conduit. The introduction of heat transfer agent into the second conduit can optionally also be run counter-current to the flow of the liquid to be cooled circulating in the first conduit.

As has been stated previously, it may be desired to be able to sterilize the fluid cooling system. For such a case, it is optionally preferred that the primary heat exchanger system also comprise a heat transfer agent recovery tank or reservoir for the heat transfer agent. Preferably, the heat transfer agent recovery tank is connected to the pump. Even more preferably, the second conduit is also connected to the heat transfer agent recovery tank, thereby forming a circuit. Optionally, the fluid cooling system can also comprise a switch connected to said second conduit to effect recovery of the heat transfer agent into the recovery tank.

As mentioned previously, the invention proposes a fluid cooling system. In the present specification and claims, the term "fluid" is intended to cover both liquids and gases. In a particularly preferred embodiment, the fluid to be cooled and dispensed is a liquid and comprises non-alcoholic beverages, such as fruit juice, water, drinking water, and alcoholic beverages, such as beer, wine, and spirit liquors. In an alternatively preferred embodiment, the fluid to be cooled and dispensed is a gas, and comprises air, oxygen, nitrogen, helium, hydrogen, nitrous oxide. Other fluids can also be envisaged, for example, biological fluids, such as blood, plasma, saline solutions, nutritive solutions, fluid pharmaceutical preparations and the like.

Optionally, but advantageously, it can be desirable to enable the fluid cooling system to be cleansed and sterilized. Accordingly, one preferred embodiment of the fluid cooling system is that the first conduit is sterilized periodically.

Another object of the invention, as mentioned briefly previously, is a cooled fluid dispenser comprising a source of fluid to be cooled and dispensed, and at least one dispenser tap, wherein the dispenser incorporates a fluid cooling system as previously defined. In particular, the cooled fluid dispenser according preferably further comprises another dispensing tap connected to the source of fluid independently from said fluid cooling system. Such second dispensing tap typically will dispense fluid that has not been cooled, that is to say, will be connected directly to the source of the fluid. This can be useful for example in beverage dispensers such as water dispensers where one can offer the choice of chilled or cooled drinking water through one dispensing tap and water at room temperature, or heated, through another dispensing tap. Preferably, the source of fluid to be cooled and dispensed is removable, and more preferably is selected from the group consisting of a pressurized or non-pressurized bottle, canister, and tank.

Yet another object of the present invention is a method for the sterilization of a fluid cooling system or a cooled fluid dispenser, comprising the following steps:
  draining a chamber carrying a heat transfer agent in a primary heat exchanger system;
  optionally draining a first conduit carrying fluid to be cooled and dispensed;
  sterilizing the first conduit for a length of time sufficient to cause bacteriological destruction and sterilization.

Still yet another object of the present invention is a method for the sterilization of a fluid cooling system or a cooled fluid dispenser, comprising the following steps:
  draining a second conduit carrying a heat transfer agent in a primary heat exchanger system;
  optionally draining a first conduit carrying fluid to be cooled and dispensed;
  sterilizing the first conduit for a length of time sufficient to cause bacteriological destruction and sterilization.

Preferably, the sterilization step in such methods comprises flushing the first conduit with a sterilizing agent, more preferably with a solution of sulfamic acid.

In a most preferred embodiment, however, the sterilization step comprises heating the first conduit to a temperature that is maintained for a time sufficient to cause bacteriological destruction and sterilization. This can be achieved by application of an electric current to substantially each end of said first conduit. In this preferred sterilization step, the heating causes any remaining fluid in the first conduit to reach sterilization temperature and travel along said conduit, thereby effecting sterilization of said conduit. Advantageously, the dispensing taps in cooled fluid dispenser are also sterilized. In another optional, yet advantageous step, a fluid source perforator connectable to a fluid source to be cooled and dispensed is also sterilized. Typically, cooled fluid dispensers such as drinking water dispensers have a removable bottle or tank as fluid source with a seal that is punctured or perforated by the perforator upon placing the fluid source on the dispenser. The perforator is generally connected to at least the first conduit, and optionally also to a second dispensing tap, and comprises a valve enabling passage of air into the tank or bottle of the fluid source, thereby ensuring that the fluid can escape from the tank or bottle into the fluid cooling system or the second dispensing tap.

The invention will now be explained in more detail with reference to the enclosed figures, which merely illustrate two preferred examples of the fluid cooling system of the present invention.

DETAILED DESCRIPTION OF THE INVENTION

Example 1

Figure 1:
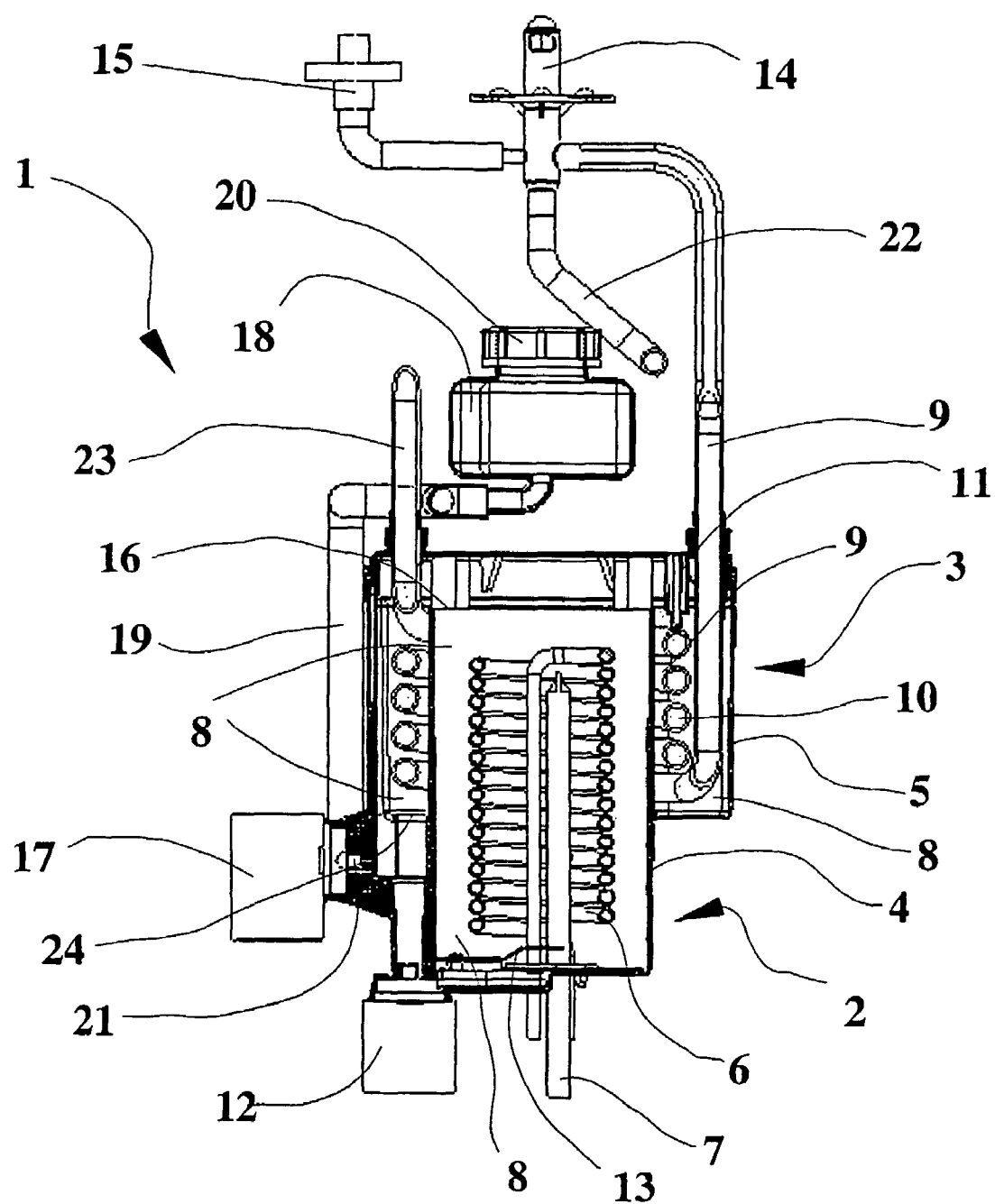
FIG. 1 represents a schematic section view of a preferred embodiment of the fluid cooling system of the present invention, including means for operating sterilization of the system.

The fluid cooling system, indicated generally by reference 1, is a machine based on an ice bank system. The system 1 comprises a primary heat exchanger system, identified generally by the reference 2, and a secondary heat exchanger system, identified generally by the reference 3. The primary and secondary heat exchangers systems 2,3 each comprise a chamber 4,5 respectively. The chambers 4,5 are made of a plastic material. Chamber 4 of the primary heat exchanger system 2 houses an evaporator or coil 6 which is connected to a standard refrigeration system (not shown) outside of the primary 2 and secondary 3 heat exchanger systems. As can be seen from the FIGS. 1 and 2 chamber 4 is partly housed within chamber 5. The chambers 4 and 5 are preferably generally cylindrical in shape. The primary heat exchanger system 2 also comprises a thermostat 7, as defined previously, designed to regulate the temperature of heat transfer agent 8, in this case water contained inside chamber 4. In chamber 4 ice as the heat transfer agent 8 in the solid phase is made by the evaporator or coil 6. The volume of ice 8 is controlled by a thermostat 7 located in the chamber close to the evaporator or coil 6.

In the secondary heat exchanger system 3, the chamber 5 houses a first conduit 9 in the shape of a stainless steel coil, which takes the fluid to be cooled 10, in this case drinking water, from a bottle (not shown) to a dispensing tap (not shown). Alternatively, the fluid to be cooled can be obtained by direct connection of the system to a distributed network of fluid, such as a tap water network. Any increase in the temperature of the drinking water 10 inside the first conduit 9 is detected by a second thermostat 11 located in the second chamber 5 next to the conduit 9. Pump 12 is activated by this second thermostat 11 and the warm heat transfer agent 8, in this case water, is drawn from the second chamber 5 via outlet 24 and pumped into the first chamber 4. This warm heat transfer agent 8 is replaced by cold heat transfer agent 8 from the first chamber 4 via outlet 16. The heat transfer agent 8 is deflected by a deflector plate 13 on its entry into the first chamber 4 in order to ensure that the heat transfer agent 8 coming from the second chamber 5, comes into contact with the solid phase heat transfer agent, i.e. the ice bank 8, to maintain the temperature of the heat transfer agent 8 at a sufficiently low level in the second chamber 5. The temperature of the fluid to be cooled 10, in this case water, inside the first conduit 9 is thereby reduced to the required level. As can be seen from FIGS. 1 and 2, a majority of the first conduit 9 is immersed in the cooling heat transfer agent 8 in the second chamber 5 of the secondary heat exchanger system 3.

One of the most efficient methods of sanitizing the fluid cooling system is to heat all the tubing used to carry the drinking water. This process is also environmentally friendly because it doesn't use any chemical products.

In the method according to the present invention, an electrical current is used to heat all the stainless steel tubing carrying the fluid to be cooled. The method involves using an electrical resistance (not shown) which is connected to an electric transformer (not shown). A high current, for example 80 A under a low voltage, for example 7.1 V travels into the secondary circuit of the transformer and a resistance. The resistance is heated by the current passing through. It will be understood that the skilled person will adapt the current and amperage to correspond to the materials used in the cooling fluid circuit and the surface area available. The temperature is determined by the length of time the current is passed through the resistance. The longer the time, the higher the temperature. In the present method, the electrical resistance is composed of the resistances of the stainless steel tube constituting the first conduit 9, optionally a perforator 14 and a part of the air circuit comprising an air filter 15, i.e. the drinking water system. Optionally, the taps mays also form part of the circuit. All these parts are linked by welding or brazing to ensure a good and continuous electrical conductivity. The dimensions of these parts are adapted to obtain the necessary electrical resistance. The fluid cooling system is connected to the electrical transformer, located outside the primary 2 and secondary 3 heat exchangers, with copper wires or other suitable material connecting two plates brazed onto the fluid cooling system. The first connection is made to the tube 15 which allows air to pass into 10 the system and the second on the first conduit 9 just before the tap. Bridging connections are also provided at different points in the circuit to close the electrical circuit and maximize the heating effect. The power of the transformer is for example about 400 W, but will be adjusted accordingly as a function of the materials used, generally between 200 W and 500 W.

In order to carry out sterilization using this apparatus, the fluid cooling system 1 is also equipped with a second pump 17, a heat transfer agent recovery or storage tank 18, a tube 19 connecting the second pump 17 to the storage tank 18, and an outlet 21 for communication of the pump with chamber 5 via outlet 24. The storage tank also comprises a plug 20 comprising a filter vent for relieving any excess pressure in the system caused by the build up of solid phase heat transfer agent 8 in chamber 4. Before sterilization can begin, pump 12 is optionally stopped, and pump 17 activated to pump out the heat transfer agent 8 from chamber 5 via outlets 24 and 21 through tube 19 to storage tank 18. Once the heat transfer agent 8 has been removed from chamber 4, the fluid source is removed, and any fluid to be cooled remaining in the first conduit 9 is evacuated either from the system via pipe 23 which leads to a dispensing tap (not shown), if an air pump is present, or else just by heating the circuit. If an air pump is present, the aim of which is decrease the time spent for sterilization, the electric current as described above can be applied, leading to heating of the first conduit 9, which in turn leads to heating of any fluid drops remaining in the first conduit 9 causing vapor to be formed or superhot gas. The temperature of this gas or vapor, is sufficient to sterilize the circuit and destroy any bacteriological infection. After sterilization, a new fluid source is placed onto the fluid cooling system, and the second pump 17 stopped, and the heat transfer agent 8 flows down via gravity from the storage tank 18 via tube 19 and via the pump and outlets 21 and 24 into chamber 5. Once the heat transfer agent 8 has been returned back into chamber 5, the pump 12 can be restarted, it was previously stopped, and operation of the cooling system can recommence. The advantage of having the second pump 17, storage tank 18 and connecting tube 19 and outlets 24 and 21 is that operational downtime is reduced since drainage and refilling of the chamber 5 is accelerated.

Figure 2:
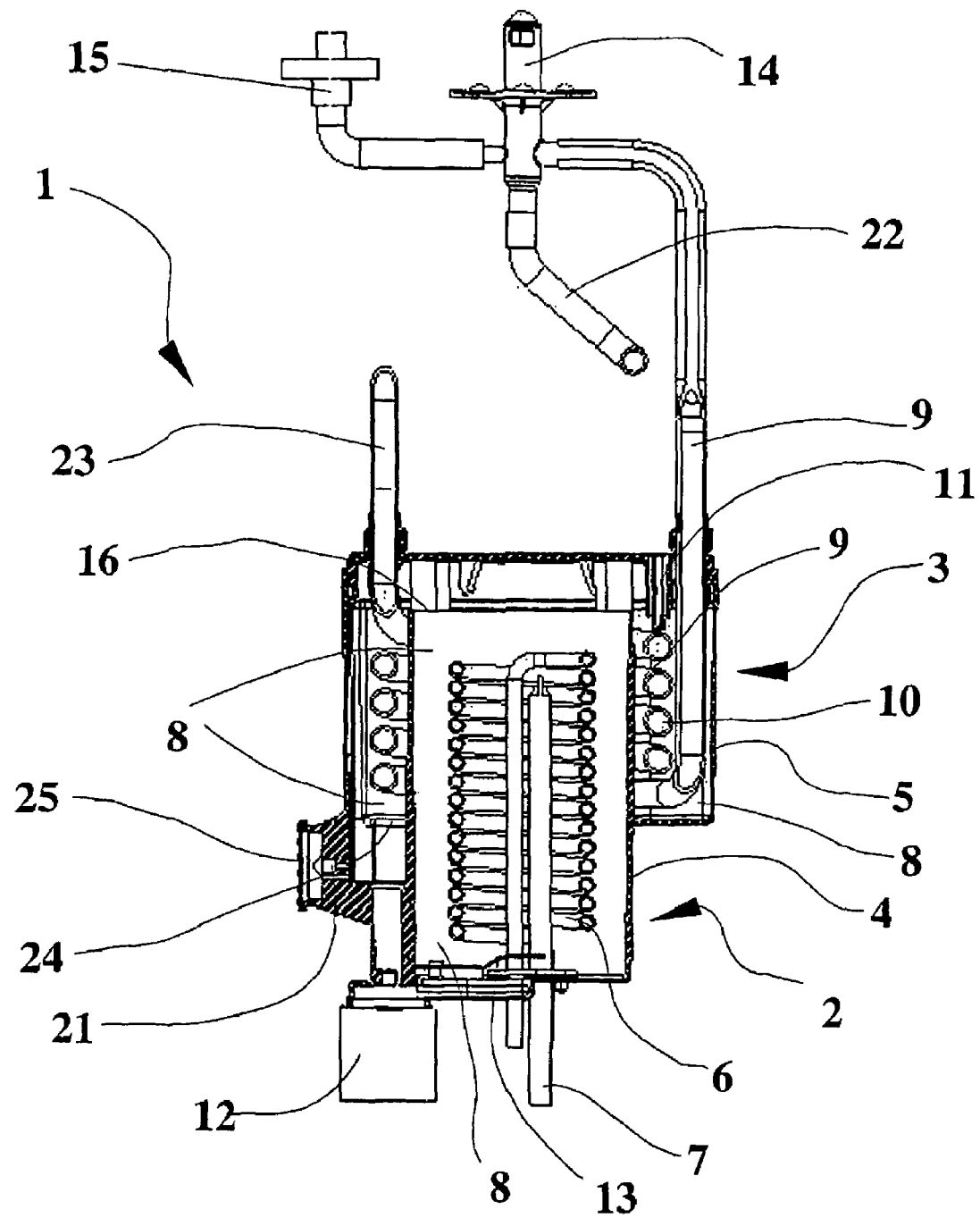
FIG. 2 represents a schematic section view of the same fluid cooling system shown in FIG. 1, except that the means for sterilization are no longer present.

The only differences of the embodiment represented in FIG. 2 with that of FIG. 1 are that the FIG. 2 embodiment does not comprise a second pump 17, storage tank 18, or connecting tube 19. The fluid cooling system does however have outlets 24 and 21, closed by a plug 25, that enable manual drainage and refilling of chamber 5, which will have to be refilled manually after any sterilization operation takes place.

Example 2

Figure 3:
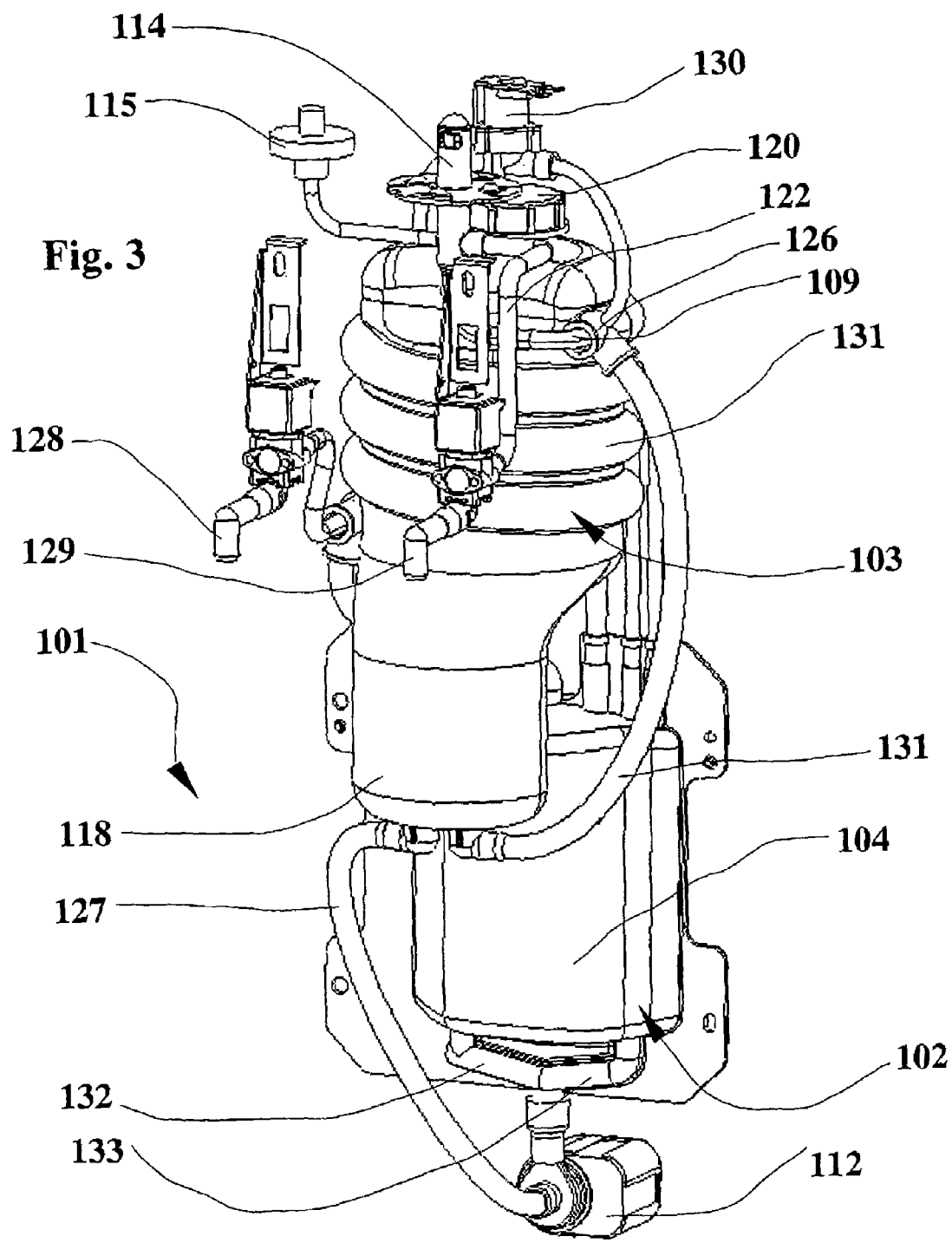
FIG. 3 represents a perspective view from the right of an alternative preferred embodiment of the fluid cooling system of the present invention.
Figure 4:
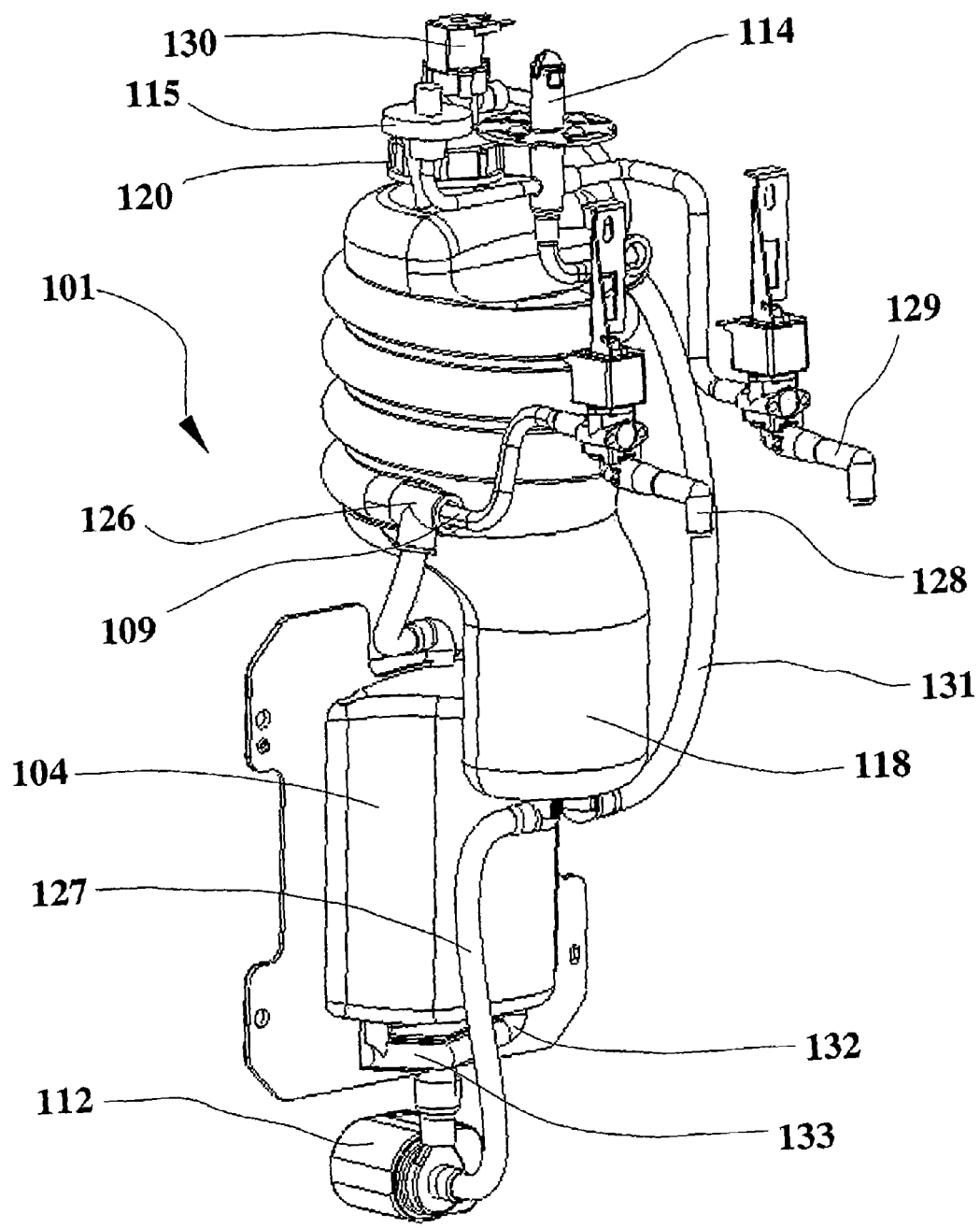
FIG. 4 represents a perspective view from the left of the same alternative embodiment of the fluid cooling system shown in FIG. 3.

The fluid cooling system, shown in FIGS. 3 and 4, and indicated generally by reference 101 comprises a primary heat exchanger, indicated generally by reference 102, a secondary heat exchanger indicated generally by reference 103, and a tank 118 that functions as a reservoir or storage tank to prime the pump 112 via tube 127 with heat exchange agent 108 and as a recovery unit for this same heat exchange agent 108.

The primary heat exchanger 102, in which cooling of the heat exchange agent occurs, comprises a tank or chamber 104, containing the heat exchange agent 108 that can be in either the fluid or solid phase around a coil (not shown), or a finger or other equivalent means known to the skilled person, but substantially as described for the preferred embodiment illustrated in FIGS. 1 and 2. The coil, in this case, is made of a suitable material that enables efficient energy transfer from the coil to the primary heat exchange agent, and is preferably made of metal, for example copper, such that the heat exchange agent 108 can pass from the fluid to the solid phase and vice-versa. The volume of the solid phase of the heat exchange agent 108 in the primary heat exchange chamber 104 is controlled by a thermostat or equivalent means well known to the skilled person, and as described for FIGS. 1 and 2. The thermostat is therefore responsible for starting and stopping the cooling operation.

The secondary heat exchanger 103 comprises a first conduit 109 within which a fluid to be dispensed circulates, for example, a beverage such as drinking water. A second conduit 126, of greater diameter than the first conduit 109, extends with and around the first conduit 109, for at least part of the length of the first conduit 109. The second conduit 126 carries the heat exchange agent 108 originating from the primary heat exchanger 102. The second conduit 126 is arranged around the conduit along its length in such a way that sufficient cooling energy is imparted by the heat exchange agent 108 to cool the fluid circulating within conduit 109. The second conduit 126 extends coaxially along substantially the whole of the length of the first conduit 109. As can be seen from FIGS. 3 and 4, the two conduits 109,126 form a generally spiral, coiled configuration 131.

The two heat exchangers 102, 103 are connected in circuit by a tank 118, that functions as a buffer tank and primer for pump, with a pump 112 that circulates the heat exchange agent 108 from the primary heat exchanger system 102 to the secondary heat exchanger system 103.

The temperature of the secondary heat exchanger 103 system is controlled indirectly by a thermostat present in the first heat exchanger system 102 or equivalent means that controls the activation of the pump 112. Preferably, the thermostat is set to activate the pump 112 as soon as fluid is withdrawn from any of the dispensing taps 128, 129. The thermostatic control of the secondary heat exchanger 103 is also used to maintain a predetermined temperature of the fluid to be dispensed.

The heat exchange agent 108 or heat transfer agent can also be retained in the tank 118 for optional cleansing of the apparatus. During cleansing, or sterilization of the first conduit 109 carrying the fluid to be dispensed, draining of the heat exchange agent 108 can be operated by opening a switch activated electromechanical valve 130 or the like. The electromechanical valve 130 sets the highest point of the first conduit 109 at the same pressure as the tank 118 and the heat exchange agent 108 then drops into the tank 118 via tube 131 and after sterilization can be transferred with the pump to the primary heat exchanger 102 via tubes 132 and 133. At this moment in time, the pump 112 is stopped.

Sterilization can be accomplished in several ways. One such way is by optionally removing the source of fluid to be cooled and dispensed, opening the dispensing taps 128, 129 and flushing the first conduit with sterilizing solution, such as a solution of sulphamic acid. This also results in removal of scale. In a particularly preferred embodiment however, the second conduit 126 is drained into the tank 118 as described previously, and then the first conduit 109 can also optionally be drained, for example by opening the dispensing taps 128, 129, leaving only trace amounts of fluid to be dispensed. The first conduit 109 can then be sterilized by application of an electrical current, as was described for the embodiment illustrated in FIG. 1 and example 1. This electrical current, which heats up the material from which the conduit is made, causes trace amounts of fluid, or any fluid, still left in the first conduit to heat up, and through alternate blocking and opening of the fluid inlet, for example with a cap, and the dispensing taps 128, 129 at the appropriate moment, it is possible to cause the hot vapor formed to travel down the circuit from the inlet to the dispensing taps 128, 129, thereby sterilizing the conduit 109. Complete sterilization of the conduit 109 can be obtained by causing electrical current to pass for sufficient time to heat up the trace amounts of fluid to a temperature sufficient to destroy enough bacteria present in the conduit 109 to a level that satisfies any necessary hygiene requirements. Generally, complete sterilization can be obtained by heating with a system as previously described after about 2 to about 10 minutes, and optionally longer. After sterilization has completed, the heat exchange agent 108 can be reintroduced into the primary and secondary heat exchangers 102, 103 by closing the electromechanical valve 130 and switching the pump 118 back on.

An alternative embodiment to this way of operating can be obtained by not providing a tank, and only incompletely filling the primary heat exchanger 102 with heat exchange agent 108. When it is desired to sterilize the conduit 109, heat exchange agent 108 is removed from the secondary heat exchanger 103 system by stopping the pump, so that heat exchange agent 108 is drawn back by gravity into the primary heat exchanger 102. In this way, when the pump 112 is stopped by the thermostat, the remaining heat exchange agent 108 in the second conduit 127 automatically drops out under the effect of gravity, thereafter permitting sterilization of the conduit 109 as described above. At this moment, it is possible to use the first conduit 109 to carry and distribute fluid at room temperature if so desired.

The invention claimed is:

1. A fluid cooling system, for use in dispensing or distributing a chilled or cooled fluid, comprising a primary heat exchanger system, a secondary heat exchanger system, a first conduit through which fluid to be cooled or chilled is circulated, and a heat transfer agent for transferring cooling energy to the fluid to be chilled circulating in the first conduit, wherein the primary and secondary heat exchanger systems are arranged at least partially one inside of another, and wherein the primary heat exchanger system comprises a chamber located substantially within a chamber of the secondary heat exchanger system, and wherein the chamber of the primary heat exchanger system has an outlet for the heat transfer agent which communicates with the chamber of the secondary heat exchanger system, and wherein the outlet of the chamber of the primary heat exchanger system is located in a wall of said chamber that is in contact with the chamber of the secondary heat exchanger system.

2. A fluid cooling system according to claim 1, wherein the primary and secondary heat exchanger system chambers are arranged substantially one inside of another.

3. A fluid cooling system according to claim 1, wherein the primary heat exchanger system chamber is arranged at least partially within the secondary heat exchanger system chamber.

4. A fluid cooling system according to claim 1, wherein the primary heat exchanger system chamber is arranged substantially within the secondary heat exchanger system chamber.

5. A fluid cooling system according to claim 1, wherein the primary heat exchanger system also comprises a coil that effects cooling thermal exchange with the heat transfer agent in the chamber of said primary heat exchanger system.

6. A fluid cooling system according to claim 1, wherein the primary heat exchanger system also comprises a thermostat.

7. A fluid cooling system according to claim 1, wherein the first conduit carrying the fluid to be cooled is located within the chamber of the secondary heat exchanger system.

8. A fluid cooling system according to claim 1, wherein the first conduit carrying the fluid to be cooled is arranged as a coil around a peripheral wall of the chamber of the primary heat exchanger system.

9. A fluid cooling system according to claim 1, wherein the fluid cooling system also comprises a reservoir for the heat transfer agent, located adjacent to the chamber of the secondary heat exchanger system.

10. A fluid cooling system according to claim 9, wherein the reservoir is located above the chamber of the secondary heat exchanger system.

11. A fluid cooling system according to claim 9, wherein the reservoir is connected to the outlet of the chamber of the secondary heat exchanger system via a pump.

12. A fluid cooling system according to claim 1, wherein the secondary heat exchanger system also comprises a pump for circulating heat transfer agent.

13. A fluid cooling system according to claim 1, wherein the primary heat exchanger system is arranged at least partially around the secondary heat exchanger system.

14. A fluid cooling system according to claim 1, wherein the primary heat exchanger system is arranged substantially around the secondary heat exchanger system.

15. A fluid cooling system according to claim 1, wherein the fluid to be cooled is a liquid.

16. A fluid cooling system according to claim 1, wherein the fluid is a liquid and comprises non-alcoholic beverages, such as fruit juice, water, drinking water, and alcoholic beverages, such as beer, wine, and spirit liquors.

17. A fluid cooling system according to claim 1, wherein the fluid to be cooled is a gas.

18. A fluid cooling system according to claim 1, wherein the fluid is a gas and comprises air, oxygen, nitrogen, helium, hydrogen, nitrous oxide.

19. A fluid cooling system according to claim 1, wherein the first conduit is sterilized periodically.

20. A cooled fluid dispenser comprising a source of fluid to be cooled and dispensed, and at least one dispenser tap, wherein the dispenser incorporates a fluid cooling system according to claim 1.

21. A cooled fluid dispenser according to claim 20, wherein the dispenser further comprises another dispensing tap connected to the source of fluid independently from said fluid cooling system.

22. A cooled fluid dispenser according to claim 20, wherein the source of fluid to be cooled and dispensed is removable.

23. A cooled fluid dispenser according to claim 20, wherein the removable source of fluid is selected from the group consisting of a pressurized or non-pressurized bottle, canister, and tank.

24. A fluid cooling system, for use in dispensing or distributing a chilled or cooled fluid, comprising a primary heat exchanger system, a secondary heat exchanger system, a first conduit through which fluid to be cooled or chilled circulated, and a heat transfer agent for transferring cooling energy to the fluid to be chilled circulating in the first conduit, wherein the primary and secondary heat exchanger systems are arranged at least partially one inside of another, and wherein the primary heat exchanger system comprises a chamber located substantially within a chamber of the secondary heat exchanger system, and wherein the chamber of the primary heat exchanger system has an outlet for the heat transfer agent which communicates with the chamber of the secondary heat exchanger system, and wherein the heat transfer agent circulates from the primary heat exchanger system to the secondary heat exchanger system via the outlet in a wall of the chamber of the primary heat exchanger system.

25. A fluid cooling system according to claim 24, wherein the primary and secondary heat exchanger system chambers are arranged substantially one inside of another.

26. A fluid cooling system according to claim 24, wherein the primary heat exchanger system chamber is arranged at least partially within the secondary heat exchanger system chamber.

27. A fluid cooling system according to claim 24, wherein the primary heat exchanger system chamber is arranged substantially within the secondary heat exchanger system chamber.

28. A fluid cooling system according to claim 24, wherein the primary heat exchanger system also comprises a coil that effects cooling thermal exchange with the heat transfer agent in the chamber of said primary heat exchanger system.

29. A fluid cooling system according to claim 24, wherein the primary heat exchanger system also comprises a thermostat.

30. A fluid cooling system according to claim 24, wherein the first conduit carrying the fluid to be cooled is located within the chamber of the secondary heat exchanger system.

31. A fluid cooling system according to claim 24, wherein the first conduit carrying the fluid to be cooled is arranged as a coil around a peripheral wall of the chamber of the primary heat exchanger system.

32. A fluid cooling system according to claim 24, wherein the fluid cooling system also comprises a reservoir for the heat transfer agent, located adjacent to the chamber of the secondary heat exchanger system.

33. A fluid cooling system according to claim 32, wherein the reservoir is located above the chamber of the secondary heat exchanger system.

34. A fluid cooling system according to claim 32, wherein the reservoir is connected to the outlet of the chamber of the secondary heat exchanger system via a pump.

35. A fluid cooling system according to claim 24, wherein the secondary heat exchanger system also comprises a pump for circulating heat transfer agent.

36. A fluid cooling system according to claim 24, wherein the primary heat exchanger system is arranged at least partially around the secondary heat exchanger system.

37. A fluid cooling system according to claim 24, wherein the primary heat exchanger system is arranged substantially around the secondary heat exchanger system.

38. A fluid cooling system according to claim 24, wherein the fluid is a liquid and comprises non-alcoholic beverages, such as fruit juice, water, drinking water, and alcoholic beverages, such as beer, wine, and spirit liquors.

39. A fluid cooling system according to claim 24, wherein the fluid to be cooled is a gas.

40. A fluid cooling system according to claim 24, wherein the fluid is a gas and comprises air, oxygen, nitrogen, helium, hydrogen, nitrous oxide.

41. A fluid cooling system according to claim 24, wherein the first conduit is sterilized periodically.

42. A cooled fluid dispenser comprising a source of fluid to be cooled and dispensed, and at least one dispenser tap, wherein the dispenser incorporates a fluid cooling system according to claim 24.

43. A cooled fluid dispenser according to claim 42, wherein the dispenser further comprises another dispensing tap connected to the source of fluid independently from said fluid cooling system.

44. A cooled fluid dispenser according to claim 42, wherein the source of fluid to be cooled and dispensed is removable.

45. A cooled fluid dispenser according to claim 42, wherein the removable source of fluid is selected from the group consisting of a pressurized or non-pressurized bottle, canister, and tank.

46. A fluid cooling system, for use in dispensing or distributing a chilled or cooled fluid, comprising a primary heat exchanger system, a secondary heat exchanger system, a first conduit through which fluid to be cooled or chilled is circulated, and a heat transfer agent for transferring cooling energy to the fluid to be chilled circulating in the first conduit, wherein the primary and secondary heat exchanger systems are arranged at least partially one inside of another, and wherein the primary heat exchanger system comprises a chamber located substantially within a chamber of the secondary heat exchanger system, and wherein the chamber of the primary heat exchanger system has an outlet for the heat transfer agent which communicates with the chamber of the secondary heat exchanger system, and wherein cooled heat transfer agent exiting via the outlet into the chamber of the secondary heat exchanger system flows into said chamber at one end of said chamber, over a peripheral surface of the first conduit, and out via an outlet in a wall of the chamber at another end of the chamber of the secondary heat exchange system.

47. A fluid cooling system, for use in dispensing or distributing a chilled or cooled fluid, comprising a primary heat exchanger system, a secondary heat exchanger system, a first conduit through which fluid to be cooled or chilled is circulated, and a heat transfer agent for transferring cooling energy to the fluid to be chilled circulating in the first conduit, wherein the primary and secondary heat exchanger systems are arranged at least partially one inside of another, and wherein the secondary heat exchanger system comprises a chamber, and wherein the fluid cooling system also comprises a reservoir for the heat transfer agent, located adjacent to the chamber of the secondary heat exchanger system, and wherein the reservoir comprises a plug comprising an excess pressure-venting membrane.

48. A fluid cooling system according to claim 47, wherein the chamber of the primary heat exchanger system has an outlet for the heat transfer agent which communicates with the chamber of the secondary heat exchanger system.

49. A fluid cooling system according to claim 47, wherein the primary and secondary heat exchanger system chambers are arranged substantially one inside of another.

50. A fluid cooling system according to claim 47, wherein the primary heat exchanger system chamber is arranged at least partially within the secondary heat exchanger system chamber.

51. A fluid cooling system according to claim 47, wherein the primary heat exchanger system chamber is arranged substantially within the secondary heat exchanger system chamber.

52. A fluid cooling system according to claim 47, wherein the primary heat exchanger system also comprises a coil that effects cooling thermal exchange with the heat transfer agent in the chamber of said primary heat exchanger system.

53. A fluid cooling system according to claim 47, wherein the primary heat exchanger system also comprises a thermostat.

54. A fluid cooling system according to claim 47, wherein the first conduit carrying the fluid to be cooled is located within the chamber of the secondary heat exchanger system.

* * * * *

UNITED STATES PATENT AND TRADEMARK OFFICE
CERTIFICATE OF CORRECTION

| | | |
|---|---|---|
| PATENT NO. | : 7,571,621 B2 | Page 1 of 1 |
| APPLICATION NO. | : 10/539911 | |
| DATED | : August 11, 2009 | |
| INVENTOR(S) | : Dietschi et al. | |

It is certified that error appears in the above-identified patent and that said Letters Patent is hereby corrected as shown below:

Column 1, line 37:

Now reads:    "SUMMERY OF THE INVENTION"

Should read:    --SUMMARY OF THE INVENTION--

Column 4, line 33:

Now reads:    "preterred embodiment"

Should read:    --preferred embodiment--

Column 8, line 5:

Now reads:    "pass into 10 the system"

Should read:    --pass into the system--

Signed and Sealed this

Sixth Day of October, 2009

David J. Kappos
*Director of the United States Patent and Trademark Office*

UNITED STATES PATENT AND TRADEMARK OFFICE
CERTIFICATE OF CORRECTION

PATENT NO. : 7,571,621 B2  
APPLICATION NO. : 10/539911  
DATED : August 11, 2009  
INVENTOR(S) : Dietschi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 489 days.

Signed and Sealed this

Seventh Day of September, 2010

David J. Kappos  
*Director of the United States Patent and Trademark Office*